United States Patent [19]

Koch

[11] Patent Number: 5,301,014

[45] Date of Patent: Apr. 5, 1994

[54] METHOD AND ARRANGEMENT FOR SPECTROSCOPICALLY MEASURING THE CONCENTRATION OF A COMPONENT OF A GAS SAMPLE

[75] Inventor: Edmund Koch, Lübeck, Fed. Rep. of Germany

[73] Assignee: Drägerwerk Aktiengesellschaft, Lübeck, Fed. Rep. of Germany

[21] Appl. No.: 858,119

[22] Filed: Mar. 26, 1992

[30] Foreign Application Priority Data

Mar. 27, 1991 [DE] Fed. Rep. of Germany ....... 4110095

[51] Int. Cl.⁵ ...................... G01N 21/31; G01N 21/39
[52] U.S. Cl. .................... 356/437; 250/343; 250/345
[58] Field of Search .............. 356/437, 250; 250/343, 250/345; 372/26, 28, 29, 31

[56] References Cited

U.S. PATENT DOCUMENTS

| | | | |
|---|---|---|---|
| 4,730,112 | 3/1988 | Wong | 250/343 |
| 4,937,461 | 6/1990 | Traina | 356/437 X |
| 5,018,155 | 5/1991 | Miyairi | 372/31 |
| 5,073,838 | 12/1991 | Ames | 372/29 X |
| 5,163,063 | 11/1992 | Yoshikawa et al. | 327/29 X |

FOREIGN PATENT DOCUMENTS 0083761  7/1983  European Pat. Off. .

OTHER PUBLICATIONS

"Measurement of gaseous oxygen using diode laser spectroscopy" by M. Kroll et al published in Applied Physics Letters, vol. 51, No. 18, Nov. 2, 1987, pp. 1465 to 1467.

Primary Examiner—Vincent P. McGraw
Attorney, Agent, or Firm—Walter Ottesen

[57] ABSTRACT

An arrangement for making gas spectroscopic measurements includes a laser diode driven by a modulated control current, a monitor diode, a detector unit for receiving a measurement signal of the transmitted radiation and a lock-in amplifier. The method utilizing the above arrangement is improved in that the offset component in the output signal of the lock-in amplifier is eliminated. This is achieved in that the radiation power of the laser diode is controlled to a pregiven modulation profile with the monitor diode functioning as an actual-value transducer.

2 Claims, 1 Drawing Sheet

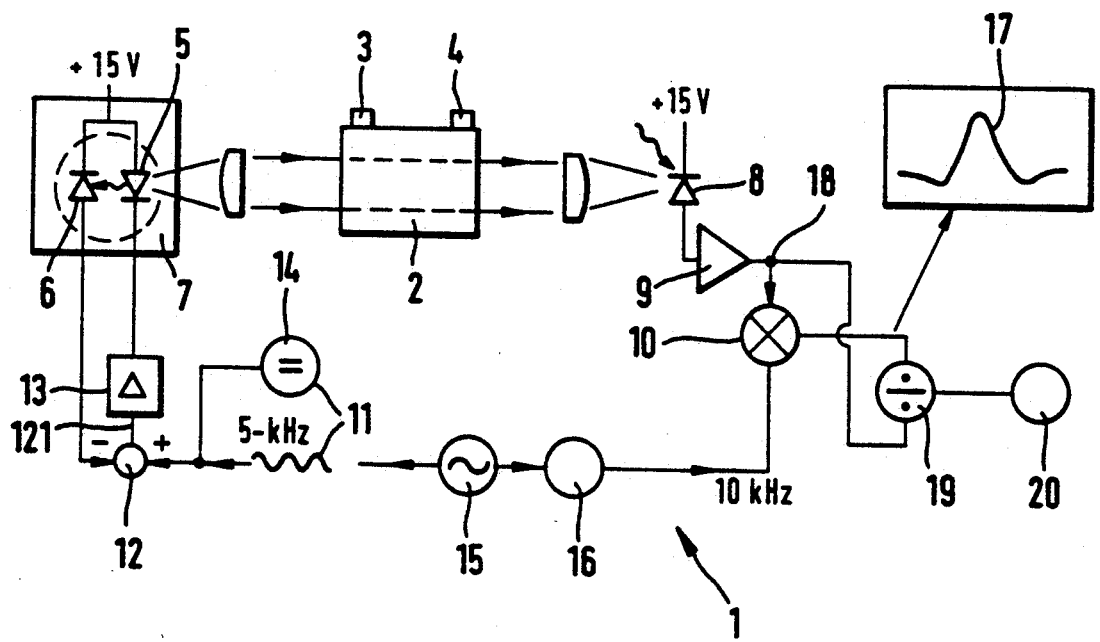

METHOD AND ARRANGEMENT FOR SPECTROSCOPICALLY MEASURING THE CONCENTRATION OF A COMPONENT OF A GAS SAMPLE

FIELD OF THE INVENTION

The invention relates to a method for spectroscopically measuring at least one component of a gas sample. The measuring arrangement for carrying out the method includes: a laser diode driven by a modulated control current for charging the gas sample with radiation in the range of an absorption line of the component, a monitor diode for detecting the radiation power of the laser diode, a detector unit for receiving a measurement signal of the transmitted radiation through the gas sample and an evaluation circuit.

BACKGROUND OF THE INVENTION

A method of the kind referred to above is disclosed in the article entitled "Measurement of gaseous oxygen using diode laser spectroscopy" in Applied Physics Letters, Volume 51, No. 18, Nov. 2, 1987, pages 1465 to 1467. The method refers to the gas spectroscopic measurement of oxygen concentrations on the basis of radiation absorption in the wavelength range of 760 to 770 nanometers. A laser diode with a monitor diode of type ML-4405 is used as a radiation source and has a wavelength range of 759 to 764 nanometers. The laser diode is supplied by a control current which is composed of a direct-current component and an alternating-current component having a frequency of 5 KHz. The operating point of the laser diode is adjusted with the direct-current component of the control current; whereas, the alternating-current component effects a periodic unbalance in the region of the absorption line. A sinusoidal-shaped curve trace is selected as the alternating current in order to drive the laser diode as harmonic free as possible. The laser diode and the monitor diode are mounted as a block on a temperature-controlled surface. The temperature of the surface brings the laser diode to one of the known absorption lines of oxygen.

The radiation emitted by the laser diode impinges on a detector unit after this radiation has passed through the gas to be investigated. The detector unit is connected to an evaluation circuit. The evaluation circuit includes essentially a lock-in amplifier having a signal input to which the measurement signal of the detector unit is applied and a reference input to which a signal voltage is applied having twice the frequency of the drive of the laser diode. Furthermore, the evaluation circuit includes a differential amplifier which likewise is connected to the measurement signal of the detector unit and receives a signal of the laser diode from the monitor diode which is proportional to the radiation power.

The output voltage of the differential amplifier corresponds to the absorption line for the measured oxygen concentration. The second derivative of the absorption line corresponds to the output signal of the lock-in amplifier. Since the absorption line is weakly pronounced especially for oxygen, this second derivative is utilized for the concentration measurement. The maximum amplitude of the output signal of the lock-in amplifier is approximately proportional to the partial pressure of the oxygen.

In the known method, it is disadvantageous that harmonic components from the current modulation of the laser diode occur because a non-linear relationship exists between the supplied radiation power and the control current of the laser diode. This non-linearity furthermore changes with the duration that the laser diode is used and effects an offset component in the output signal of the lock-in amplifier. In order to carry out a measurement, this offset, which is also dependent upon time, must be compensated by making an adjustment with a reference gas of known concentration. This is complex and affects the possibilities of utilizing a measuring system of this kind.

Published European patent application 0,183,761 discloses a photometric measuring arrangement wherein the radiation emanating from a measuring cell and from a reference measuring cell are received by separate detectors and the measurement signals of the detectors are supplied to an evaluation circuit. The detectors are additionally irradiated by a reference light source having modulated light whereby a second measuring signal is produced. The second measuring signal is, on the one hand, applied for making the detectors symmetrical in that the amplifier component of a detector is automatically tracked and, on the other hand, for adjusting the static radiation power of the reference light source. The radiation power of the reference light source is referred to a constant reference voltage source. The closed-loop control of the radiation power to a pregiven modulation profile is however not disclosed in this published European patent application.

SUMMARY OF THE INVENTION

It is an object of the invention to improve a method for the spectroscopic measurement of a gas in that the offset component in the output signal of the lock-in amplifier is eliminated.

The method of the invention is for spectroscopically measuring at least one component of a gas sample. The method includes the steps of: generating radiation in the region of an absorption line of the component with a laser diode driven by a modulated control current; transilluminating the gas sample with the radiation; detecting the energy of the radiation with a monitor diode which produces a measuring signal; controlling the energy of the radiation to a pregiven modulation profile by utilizing the measuring signal of the monitor diode as an actual value; detecting the radiation passed through the gas sample and forming a detector signal indicative thereof; and, evaluating the detector signal in an evaluation circuit for determining the concentration of the component in the gas sample.

The advantage of the invention is seen essentially in that non-linear components in the emitted radiation are eliminated by means of the control of the radiation power of the laser diode to the pregiven modulation profile. This is achieved because the monitor diode detects the actual value of the radiation power and possible deviations from the modulation profile are compensated by a corresponding drive of the laser diode. Since the curve trace of the radiation power of the laser diode is controlled to the pregiven modulation profile, harmonic components no longer occur in the frequency spectrum and the offset component therefore disappears in the output signal of the lock-in amplifier. Since a control principle of the above kind is independent of the aging characteristic of the laser diode, a compensation of the offset component over the entire service life of the laser diode is ensured. Experiments have shown that an improved signal-to-noise ratio in the output signal of the lock-in amplifier is achieved with the features of the invention. This is especially significant for the measurement of the oxygen concentration since here, the operation is at lower signal levels.

It is advantageous to select the modulation profile so that it comprises a direct-voltage component and a sinusoidally-shaped alternating-voltage component superposed thereon.

For carrying out the method of the invention, it is advantageous to connect the laser diode to a control device to which the pregiven modulation profile is applied as a desired value and to which the measurement signal of the monitor diode is applied as an actual value.

BRIEF DESCRIPTION OF THE DRAWING

The invention will now be described with reference to the single figure of the drawing which is a circuit diagram of the arrangement according to the invention for spectroscopically measuring the concentration of a gas component.

DESCRIPTION OF THE PREFERRED EMBODIMENTS OF THE INVENTION

The drawing shows a measuring system 1 for making gas spectroscopic measurements of the oxygen concentration of a gas sample. The gas sample is located in a measurement cuvette 2 and flows therethrough from a cuvette inlet 3 to a cuvette outlet 4. The measurement cuvette 2 is transilluminated by a laser diode 5. The laser diode 5 together with a monitor diode 6 is attached to a temperature-controlled surface 7. The radiation passing out of the cuvette 2 impinges upon a detector unit 8 and the measurement signal produced by the detector is applied via an amplifier 9 to a lock-in amplifier 10 operating as an evaluation circuit. The drive of the laser diode 5 is produced by means of a modulation profile 11 which is composed of a direct voltage from a direct-voltage source 14 and a sinusoidally-shaped alternating voltage having the frequency 5 KHz. The alternating voltage is generated in a generator 15. The modulation profile 11 as a desired value reaches a comparator 12 which receives the measurement signal of the monitor diode 6 as an actual value. The output line 121 of the comparator 12 is connected to a control unit 13 which generates the control current for the laser diode 5 and which controls the radiation power to the modulation profile 11.

The sinusoidally-shaped alternating voltage of the generator 15 is conducted via a frequency doubler 16 and is then supplied to the lock-in amplifier 10. The output signal 17 of the lock-in amplifier 10 corresponds to the second derivative of the absorption signal for the oxygen concentration in the gas sample. The output signal 17 and the signal at the measurement point 18 are connected to a divider 19 which is connected to a display unit 20 for the oxygen concentration. A normalization is achieved with the divider 19 in such a manner that intensity losses of the radiation are compensated.

These intensity losses can, for example, be attributed to a contamination of the cuvette 2.

It is understood that the foregoing description is that of the preferred embodiments of the invention and that various changes and modifications may be made thereto without departing from the spirit and scope of the invention as defined in the appended claims.

What is claimed is:

1. An arrangement for spectroscopically measuring at least one component of a gas sample, the arrangement comprising:

laser means for passing radiation through the gas sample with said radiation being in the region of an absorption line of said component;

monitor means for detecting the actual radiation energy of said laser means and for converting said radiation energy into a measuring signal;

modulation profile means for generating a pregiven modulation profile signal;

said modulation profile means including: direct-voltage means for supplying a direct voltage; and, alternating-voltage generator means for generating a sinusoidally-shaped alternating voltage superposed on said direct voltage thereby defining said pregiven modulation profile signal;

control means receiving said measuring signal as an actual value and said modulation profile signal as a desired value for generating a modulated drive current in dependence upon the difference of said values;

detector means for receiving the radiation passed through said gas sample and for supplying a detector signal in dependence upon the detected radiation; and, evaluation means for receiving and evaluating said detector signal to determine the concentration of said component.

2. A method for spectroscopically measuring at least one component of a gas sample, the method comprising the steps of:

generating radiation in the region of an absorption line of the component with a laser diode driven by a modulated control current;

transilluminating the gas sample with said radiation;

detecting the energy of said radiation with a monitor diode which produces a measuring signal;

generating a modulation profile signal from a direct-voltage component and a sinusoidally-shaped alternating voltage superposed on said direct-voltage component thereby defining a pregiven modulation signal;

controlling the energy of said radiation to said pregiven modulation profile signal as a desired value by utilizing said measuring signal of said monitor diode as an actual value;

detecting said radiation passed through the gas sample and forming a detector signal indicative thereof; and, evaluating said detector signal in an evaluation circuit for determining the concentration of said component in said gas sample.

* * * * *